United States Patent [19]

Katsurada et al.

[11] Patent Number: 5,217,002
[45] Date of Patent: Jun. 8, 1993

[54] FLEXIBLE TUBE OF ENDOSCOPE AND METHOD OF PRODUCING THE SAME

[75] Inventors: Hiroyuki Katsurada; Wataru Murai, both of Tokyo, Japan

[73] Assignee: Asahi Kogaku Kogyo Kabushiki Kaisha, Tokyo, Japan

[21] Appl. No.: 694,374

[22] Filed: May 1, 1991

[30] Foreign Application Priority Data

May 14, 1990 [JP] Japan .................. 2-124484

[51] Int. Cl.$^5$ .............................. A61B 1/00
[52] U.S. Cl. ........................................ 128/4
[58] Field of Search ........................ 128/4, 6

[56] References Cited

U.S. PATENT DOCUMENTS 3,674,014  7/1972  Tillander .

FOREIGN PATENT DOCUMENTS

| 1893615 | 3/1964 | Fed. Rep. of Germany . |  |
|---|---|---|---|
| 3436288 | 4/1986 | Fed. Rep. of Germany | 128/6 |
| 3926320 | 3/1990 | Fed. Rep. of Germany | 128/6 |
| 55-118730 | 9/1955 | Japan | 128/4 |
| 56-68426 | 6/1956 | Japan | 128/4 |
| 58-86129 | 5/1958 | Japan | 128/4 |
| 61-168326 | 7/1961 | Japan | 128/4 |
| 54-159792 | 11/1979 | Japan | 128/4 |
| 56-101301 | 8/1981 | Japan | 128/4 |
| 64-45817 | 3/1989 | Japan | 128/6 |
| 2045964 | 11/1980 | United Kingdom . |  |

OTHER PUBLICATIONS

English Language Abstracts of Japan Patent Nos. 54-159,792, 55-118,730, 56-68,426, 56-101-301, 58-86,129, 61-168,326 and 64-45,817.

Primary Examiner—Gene Mancene
Assistant Examiner—Thomas Price
Attorney, Agent, or Firm—Sandler Greenblum & Bernstein

[57] ABSTRACT

A long and thin flexible tube of an endoscope which forms an outer wall of an insert part and which is fitted with a built-in object including a device for transmitting an observed image from the distal end of the insert part to the proximal end thereof. Also disclosed is a method of producing the long and thin flexible tube. The flexible tube is formed by inserting the built-in object into a plurality of short flexible tube elements, and then connecting together each pair of adjacent short flexible tube elements by use of a connecting device, with the built-in object inserted therein.

15 Claims, 9 Drawing Sheets

FLEXIBLE TUBE OF ENDOSCOPE AND METHOD OF PRODUCING THE SAME

The present disclosure relates to subject matter contained in Japanese patent application No. 2-124484 (filed on May 14, 1990), which is expressly incorporated herein by reference in its entirety.

BACKGROUND OF THE INVENTION

1. Field of the Invention

The present invention relates to a long and thin flexible tube of an endoscope which is fitted with a built-in object, for example, a device for transmitting an observed image. The present invention also relates to a method of producing such a long and thin flexible tube.

With the recent development of the endoscopic technology, there has been an increasing need for considerably long insert parts in medical endoscopes which are used to observe the inside of the small intestine, and also for industrial endoscopes. Small-intestine, endoscopes need insert parts with an overall length of about 4 m to 7 m, and industrial endoscopes need much longer ones, i.e., even an insert part with an overall length of from 30 m to 50 m.

2. Description of the Prior Art

Figure 9:
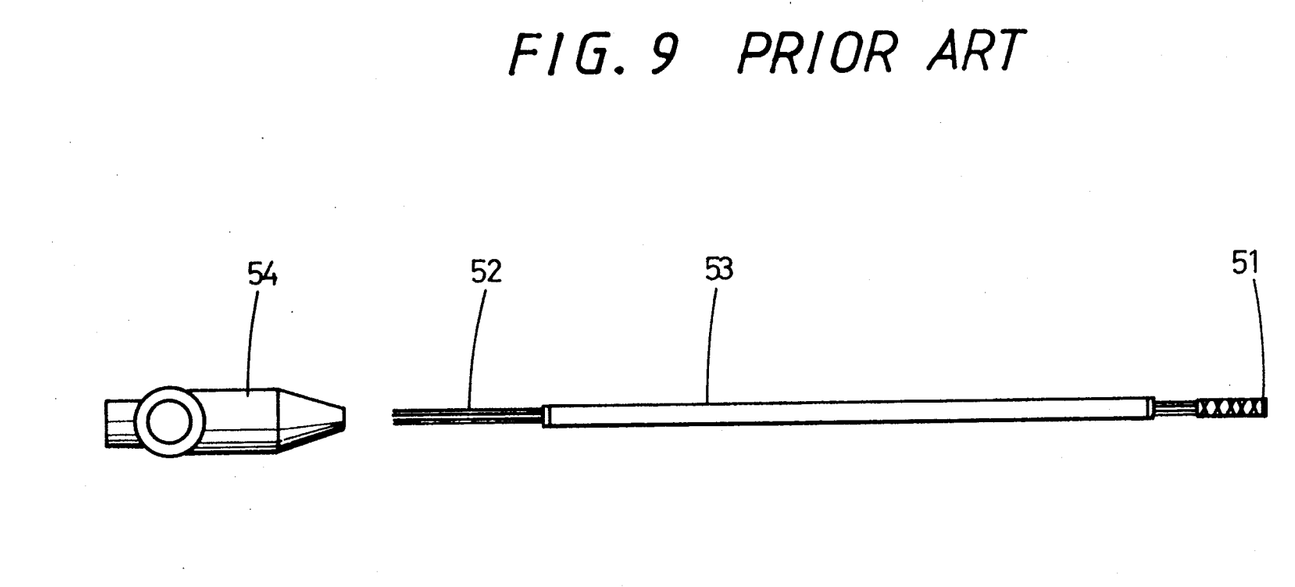
FIG. 9 is a side view of a conventional flexible tube which is in the assembling process.

FIG. 9 shows a typical conventional endoscope which is in the process of being assembled. Reference numeral 51 denotes a distal end part that incorporates an objective optical system and other elements, 52 a built-in object such as an image guide fiber bundle, 53 a flexible tube, and 54 a control part.

As shown in FIG. 9, the conventional flexible tube 53 is formed in advance as a single flexible tube with a uniform or locally varied hardness, and the built-in object 52 is inserted into the flexible tube 53 to assemble the endoscope.

Such an assembling method involves no serious problem as long as the overall length of the flexible tube 53 is less than about 2 m. However, when the overall length of the flexible tube is increased by a large margin as in the case of small-intestine endoscopes and industrial endoscopes, which have recently needed to have considerably long insert parts, the frictional resistance that occurs when a built-in object is inserted into the long flexible tube increases so that it becomes difficult to insert the built-in object. There is therefore a danger that the built-in object or the flexible tube itself may break during the inserting operation.

SUMMARY OF THE INVENTION

An object of the present invention is to provide a flexible tube of an endoscope which is designed so that even if the flexible tube is considerably long, a built-in object can be readily inserted therein to assemble the endoscope, and also a method of producing such a flexible tube.

Other objects and advantages of the present invention will become apparent from the following detailed description of illustrated embodiments of the invention.

According to the present invention, a flexible tube of an endoscope which forms an outer wall of an insert part and which is fitted with a built-in object, including a device for transmitting an observed image from the distal end of the insert part to the proximal end thereof, comprises: a plurality of flexible tube elements; and a device for connecting together each pair of adjacent flexible tube elements with the built-in object inserted therein to form the flexible tube.

In addition, a method of producing a flexible tube of an endoscope which forms an outer wall of an insert part and which is fitted with a built-in object, including a device for transmitting an observed image from the distal end of the insert part to the proximal end thereof, comprises: inserting the built-in object into a plurality of flexible tube elements; and connecting together each pair of adjacent flexible tube elements by use of a connecting device, with the built-in object inserted therein, to form a single flexible tube.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
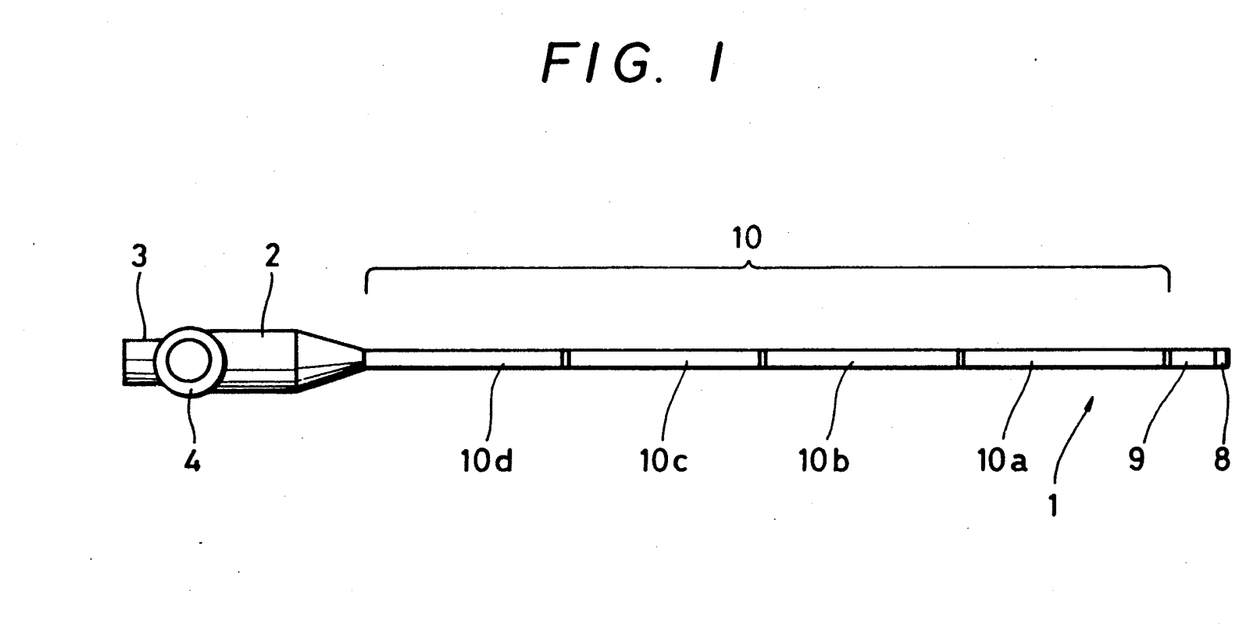
FIG. 1 is a side view of an endoscope according to a first embodiment of the present invention.

Referring to FIG. 1, reference numeral 1 denotes an insert part of an endoscope, 2 a control part, and 3 an eyepiece.

The insert part 1 comprises a distal end part 8 that incorporates an objective optical system and other elements (not shown), a bendable portion 9 that is bendable by remote control effected by a control handle 4 that is provided on the control part 2, and a long and thin flexible tube 10.

In addition, a built-in object, such as an image guide fiber bundle for transmitting an observed image that is formed by the objective optical system, extends through the bendable portion 9 and the flexible tube 10 over the whole length.

The flexible tube 10 forms the outer wall of the insert part 1. The flexible tube 10 has an overall length of 6 m, for example, and comprises four short flexible tube elements 10a, 10b, 10c and 10d, each having a length of 1.5 m.

Figure 2:
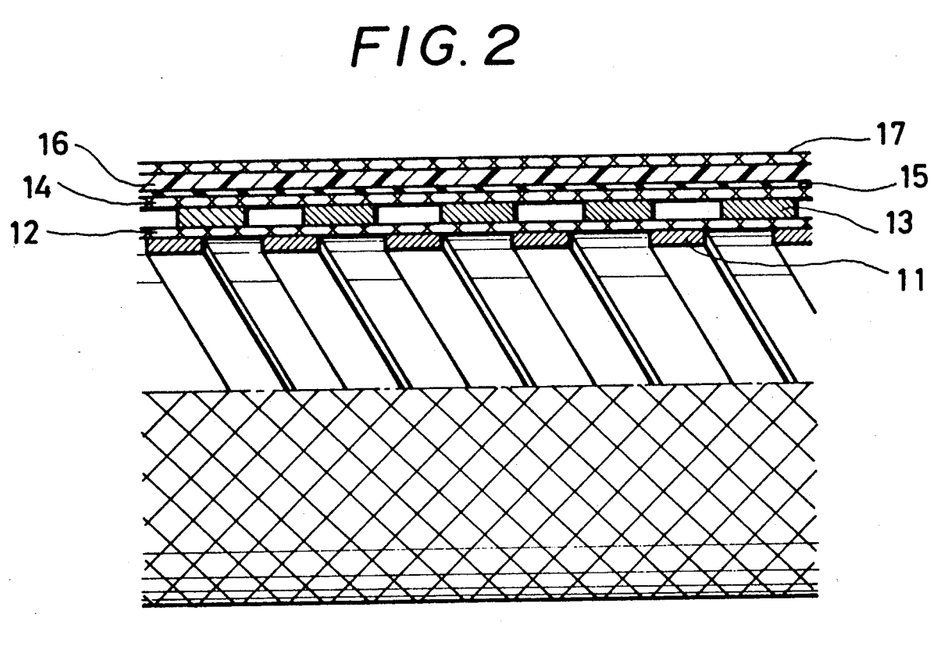
FIG. 2 is a fragmentary enlarged sectional side view of a flexible tube according to the first embodiment of the present invention.

FIG. 2 shows the arrangement of a tube portion of a flexible tube that is suitable for an industrial endoscope.

A first metallic spiral tube 11 forms the innermost layer of the flexible tube, and the following tubes are successively provided outside the spiral tube 11: a first metallic braid tube 12, a second spiral tube 13 which is wound in the reverse direction to the first spiral tube 11, a second metallic braid tube 14, a thermoplastic, thermosetting or ultraviolet-curing elastomer 15, a heat-shrinkable synthetic resin tube 16 which is superior in heat resistance, radiation resistance and oil resistance, and a third metallic braid tube 17.

Examples of materials which are usable as the elastomer 15 include fluororubber, silicone resin, urethane resin, acrylic resin, etc. Examples of materials usable for the heat-shrinkable synthetic resin tube 16 include a silicone resin, fluorocarbon resin, fluororubber, etc. The third braid tube 17, which forms the outermost layer, may be impregnated with a synthetic resin material or an elastomer, for example, a rubber material, according to the use and application.

Figure 3:
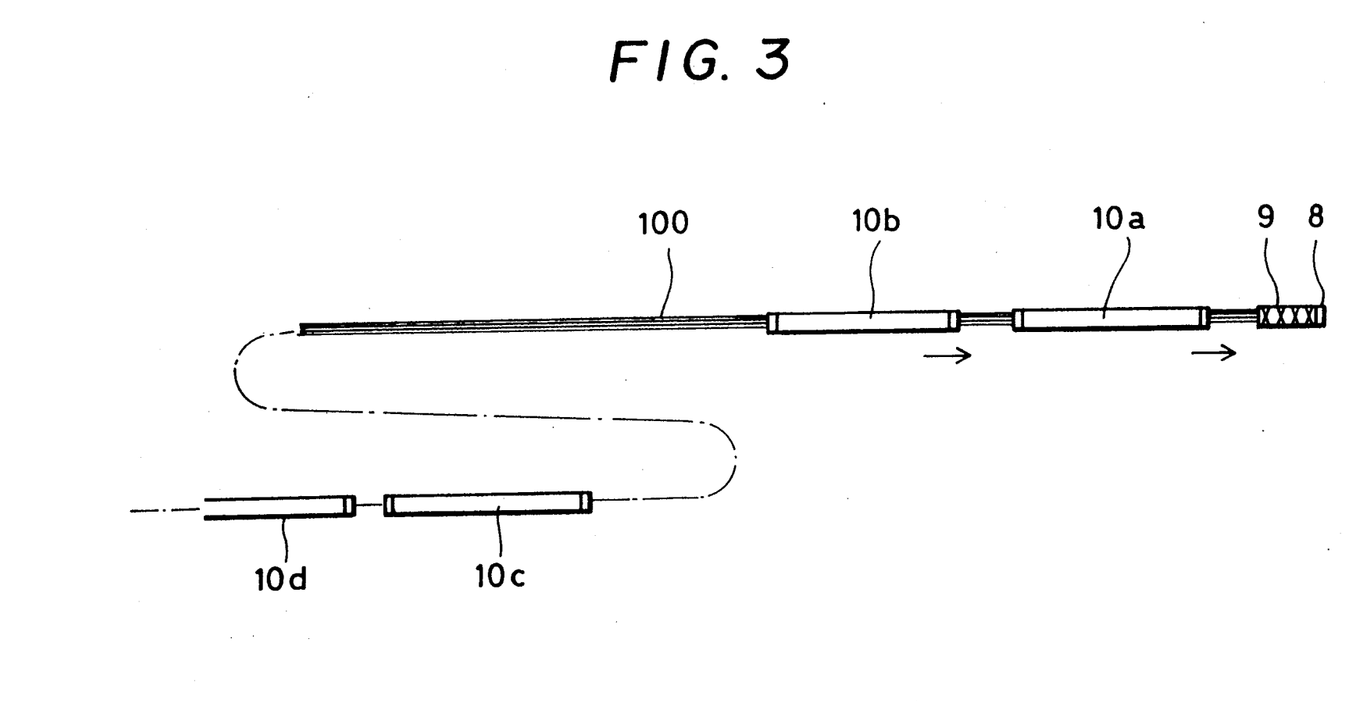
FIG. 3 is a side view of the flexible tube according to the first embodiment of the present invention, which is in the assembling process.

FIG. 3 shows the manner in which a built-in object 100 is inserted into the flexible tube 10 to assemble the endoscope. The built-in object 100 includes an illuminating light guide fiber bundle and various tubes in addition to the image guide fiber bundle. In the case of an endoscope that employs a solid-state image sensor in place of the image guide fiber bundle to transmit an image, electric wires are added to the built-in object 100.

As shown in FIG. 3, the built-in object 100 is not inserted into the short flexible tube elements 10a to 10d previously connected together in the form of a single flexible tube, but is successively inserted into the short flexible tube elements 10a to 10d which are separate from each other. After the built-in object 100 has been inserted, each pair of adjacent short flexible tube elements 10a to 10d are connected together to form a long and thin flexible tube 10 such as that shown in FIG. 1.

Figure 4:
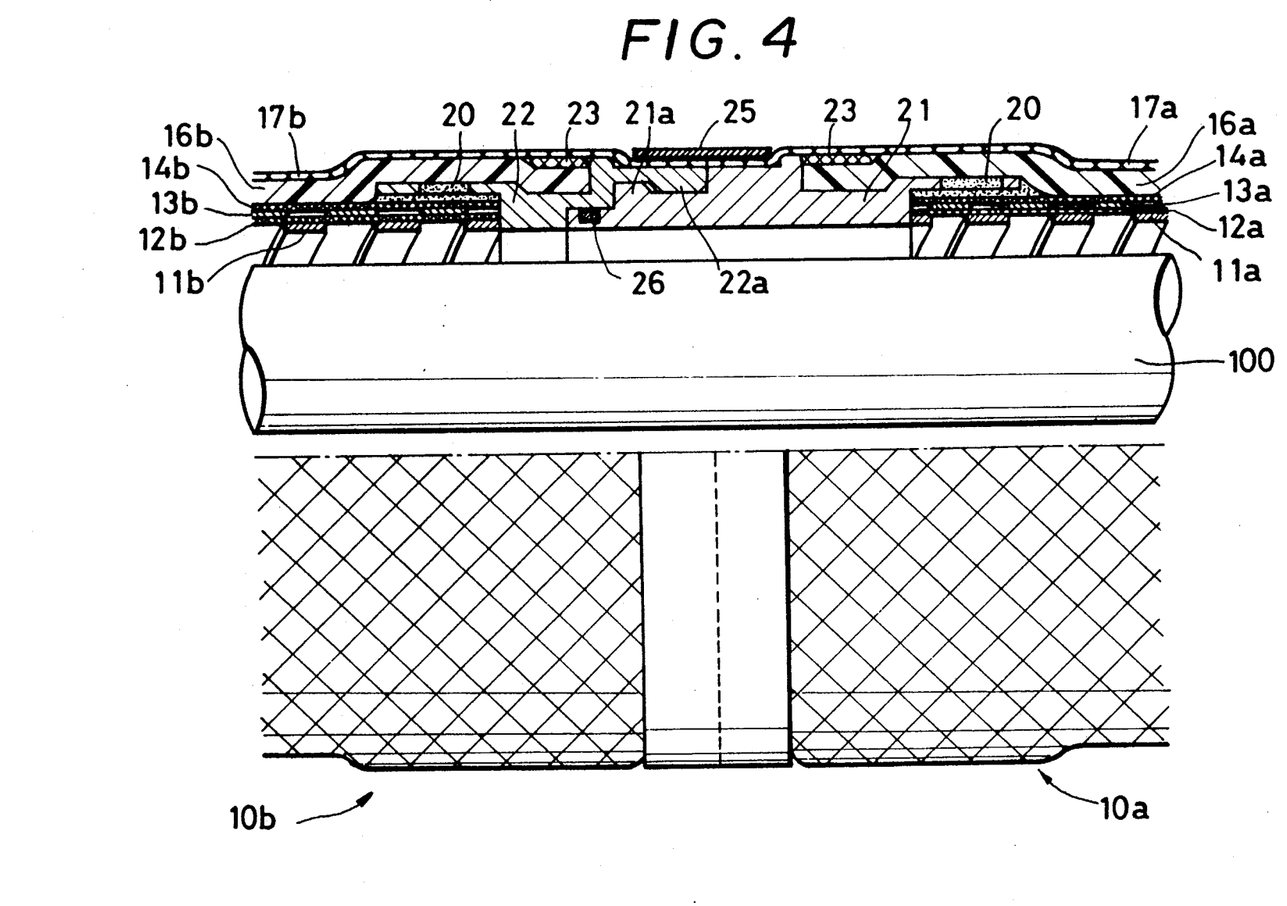
FIG. 4 is a fragmentary enlarged sectional side view of a joint of the flexible tube according to the first embodiment of the present invention.

FIG. 4 shows a joint of a pair of short flexible tube elements 10a and 10b. It should be noted that these flexible tube elements 10a and 10b are provided with no elastomer layer.

The first and second short flexible tube elements 10a and 10b respectively have a male female coupling member 22 which have previously been secured to their respective end portions by high-temperature solder 20 or the like. In addition, the end portions of the heat-shrinkable tubes 16a and 16b of the flexible tube elements 10a and 10b are tied tightly with thread 23 before being coated with an adhesive. As the thread 23, nylon, silk thread, cotton thread, etc. may be employed.

Figure 5:
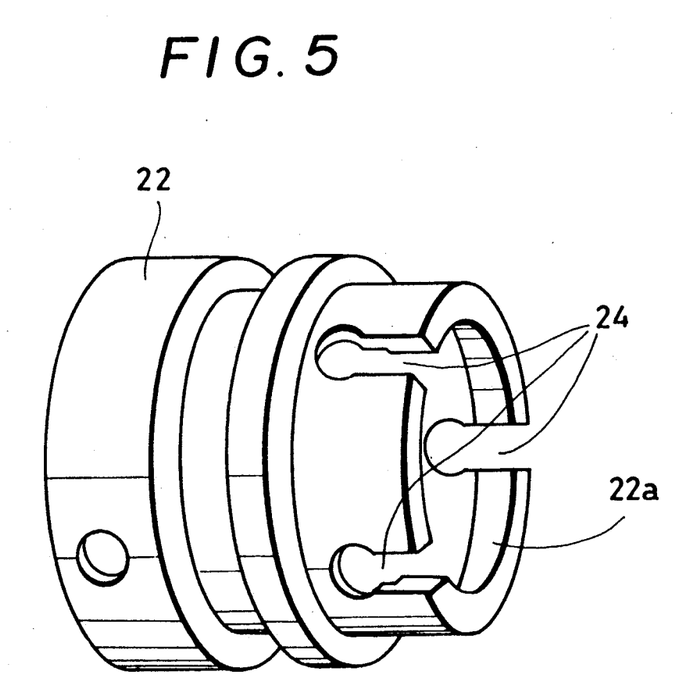
FIG. 5 is a perspective view of a female coupling member according to the first embodiment of the present invention.

As shown in FIG. 5, the open end portion of the female coupling member 22 is provided with a plurality of circumferentially spaced axial slits 24. The male coupling member 21 has an outwardly extending annular projection 21a which is formed on the outer periphery of its open end portion, and the female coupling member 22 has an inwardly extending annular projection 22a which is formed on the inner periphery of its open end portion.

Accordingly, when the male coupling member 21 is axially forced into the female coupling member 22, the respective end portions of the projections 21a and 22a of the two coupling members 21 and 22 come into contact with each other, causing the mouth portion of the female coupling member 22 to expand by elastic deformation, thus resulting in the male coupling member 21 being inserted into the female coupling member 22. When the male coupling member 21 is inserted sufficiently deep in the female coupling member 22 to a predetermined position, the projections 21a and 22a of the two coupling members 21 and 22 reach each other's rear portions. As a result, the mouth portion of the female coupling member 22 is restored to its previous shape, thereby enabling the two coupling members 21 and 22 to engage each other so that these members 21 and 22 will not disengage undesirably, as shown in FIG. 4.

The joint of the two coupling members 21 and 22 is covered with a metallic decorative ring 25, which has a sealing material or the like coated on its inner surface. In addition, the joint of the two coupling members 21 and 22 is sealed with an O-ring 26 so that no water or other liquid can enter the inside from the outside.

Thus, the short flexible tube elements 10a, 10b, 10c and 10d can be successively connected to each other with the built-in object 100 inserted therein. The short flexible tube elements 10a to 10d, which are connected together, can be separated from each other by axially pulling them in the reverse direction from that described above. Accordingly, the assembly and replacement of the flexible tube 10 can be effected with ease. If the inner surface of the decorative ring 25 is coated with an adhesive, only the ring 25 may be destroyed when the flexible tube 10 is disassembled.

Figure 6:
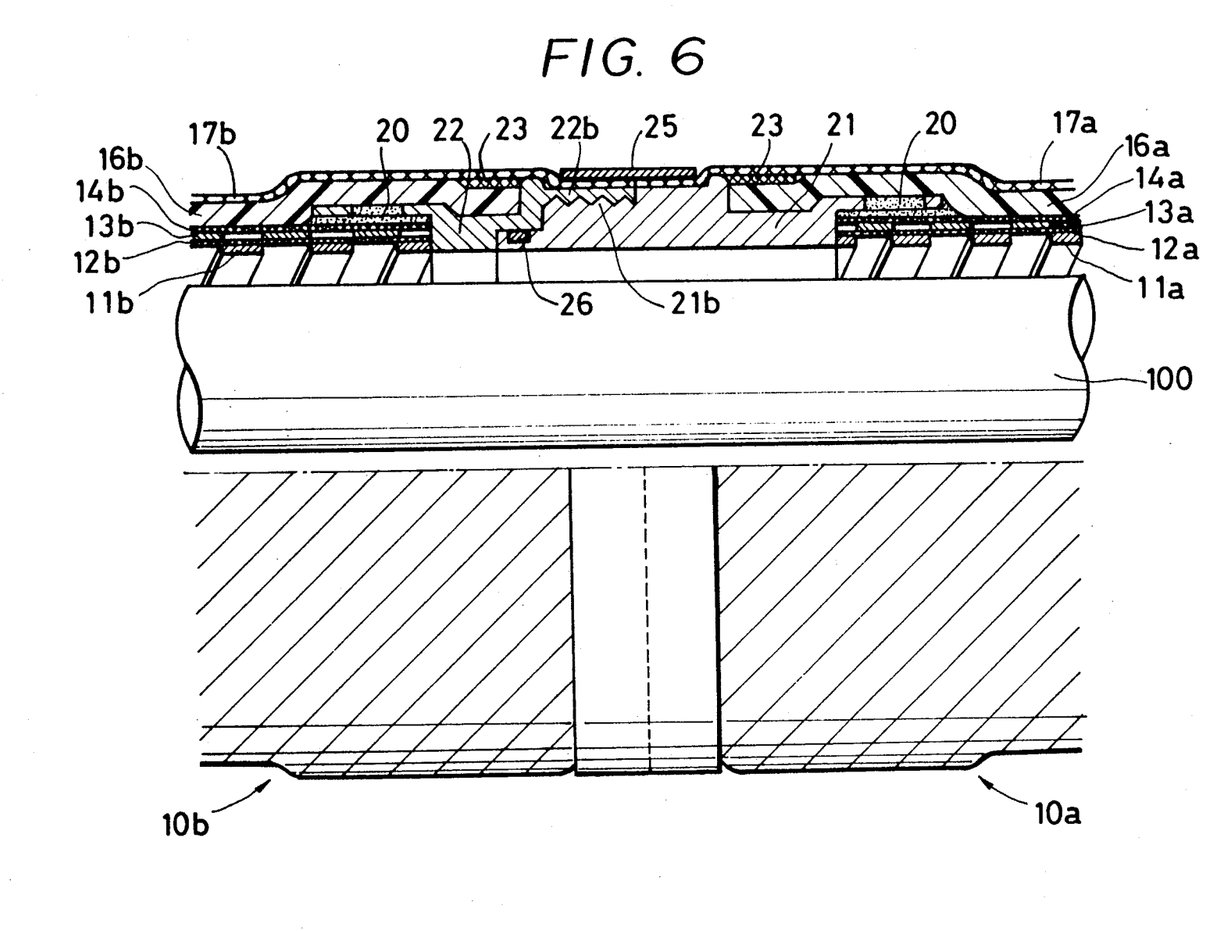
FIG. 6 is a fragmentary enlarged sectional side view of a joint of the flexible tube according to a second embodiment of the present invention.

FIG. 6 shows a second embodiment of the present invention, in which both the male and female coupling members 21 and 22 are formed with threads 21b and 22b to connect them by thread engagement. Accordingly, the two coupling members 21 and 22 are connected and disconnected by rotating them relative to each other about their axis. Preferably, the thread-engaged portions are coated with a sealing material and bonded together to such an extent that the coupling members 21 and 22 can be disassembled. Alternatively, the thread-engaged portions may be bonded to each other with an adhesive which is soluble in a specific solvent. In the other respects, the second embodiment is the same as the first embodiment described above.

Figure 7:
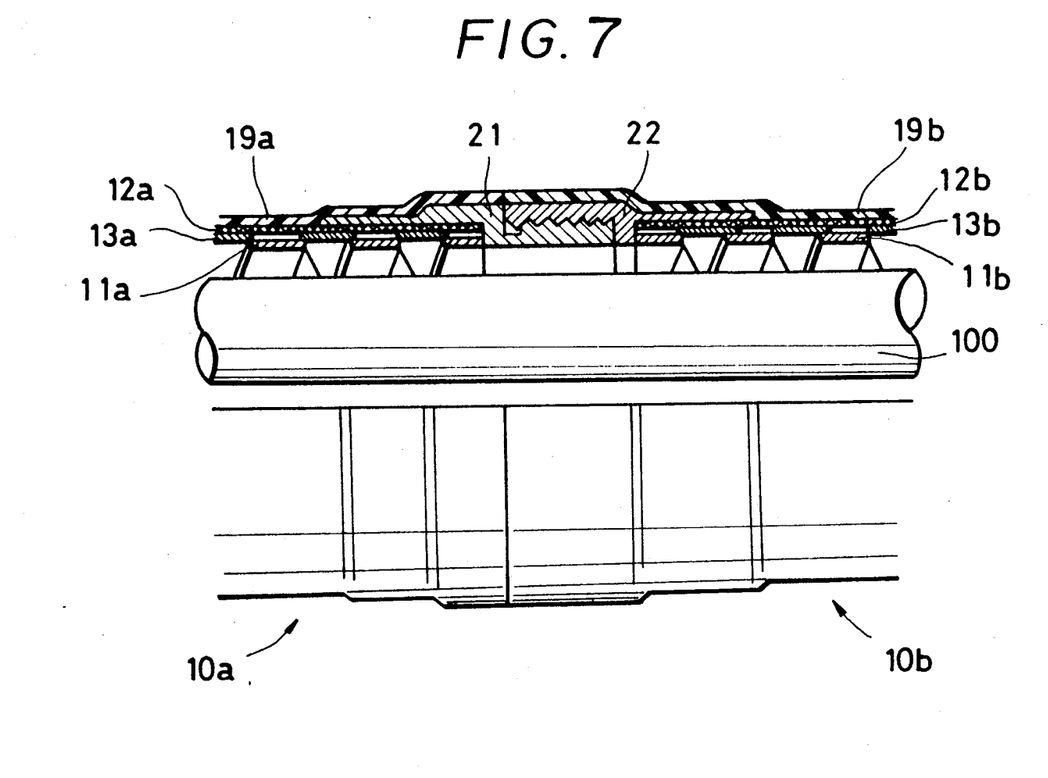
FIG. 7 is a fragmentary enlarged sectional side view of a joint of the flexible tube according to a third embodiment of the present invention.

FIG. 7 shows a third embodiment of the present invention, which is suitable for medical endoscopes, for example, small-intestine endoscopes.

In this embodiment, short flexible tube elements 10a and 10b comprise, respectively, first spiral tubes 11a and 11b, second spiral tubes 13a and 13b, and braid tubes 12a and 12b, which are provided successively in order from the inner side. In addition, the outermost layers of the short flexible tube elements 10a and 10b are covered with respective skin tubes 19a and 19b, which are made of a polyurethane resin material. The skin tubes 19a and 19b also cover the outer peripheries of the coupling members 21 and 22. The coupling members 21 and 22 are connected together by thread engagement in the same way as in the second embodiment. The mating surfaces of the skin tubes 19a and 19b are bonded to each other.

In the case of a medical endoscope, it is necessary, in order to reduce the pain that is inflicted on the patient, to minimize the diameter of the insert part and also minimize the length of an inflexible portion. In the flexible tube of the third embodiment, the outer diameter of the joint is a little larger than in the first and second embodiments and some inflexible portions are inevitably made. However, since the flexible tube itself is very long, the increase in the outer diameter and the increase in the length of inflexible portions are negligible, considering the length of the flexible tube. Accordingly, no extra pain is inflicted on the patient.

Figure 8:
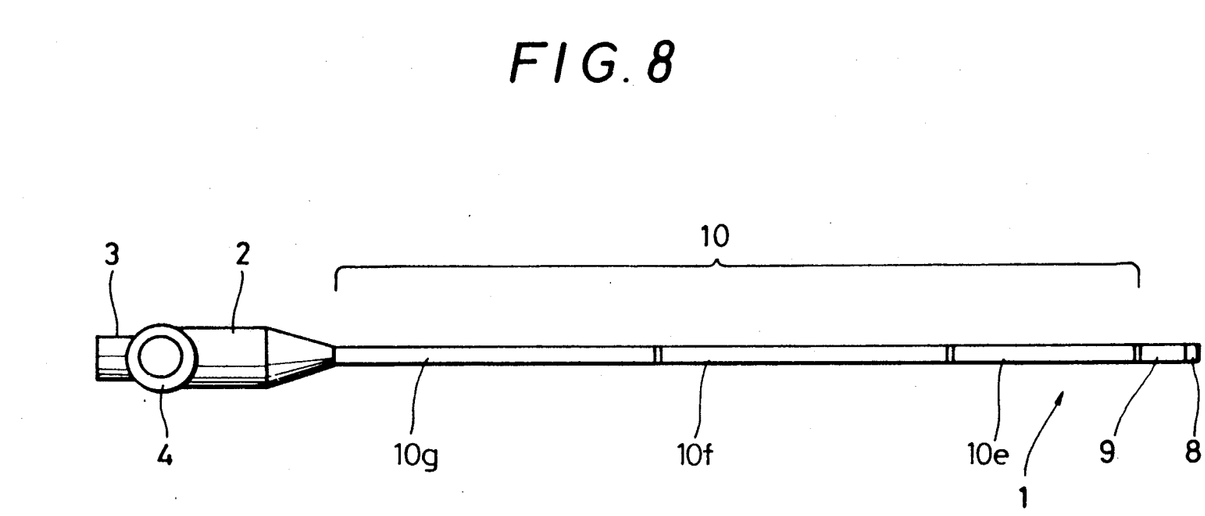
FIG. 8 is a side view of an endoscope according to a fourth embodiment of the present invention.

FIG. 8 shows a fourth embodiment of the present invention, in which the flexible tube 10 comprises, for example, three short tube elements; that is, a distal tube element 10e which is flexible, a proximal tube element 10g which is rigid, and an intermediate tube element 10f with a hardness which is intermediate between those of the two tube elements 10e and 10g. A built-in object is inserted into the short flexible tube elements 10e, 10f and 10g which are separate from each other, and then each pair of adjacent short flexible tube elements 10e to 10g are connected together to form a long and thin flexible tube 10.

The hardness of the flexible tube 10 can be varied, for example, by varying the width of the spiral tubes 11 and 13, the material of the elastomer 15, the grade of the heat-shrinkable tube 16, or the grade of the polyurethane resin material that is employed to form the skin tube 19.

In this way, it is possible to readily produce a long flexible tube which is locally varied in hardness in accordance with the use and application.

According to the present invention, a built-in object is successively inserted into a plurality of short flexible tube elements, which are separate from each other, to assemble a flexible tube. Accordingly, even a considerably long flexible tube can be readily assembled without breaking the built-in object or the flexible tube itself. In addition, if the flexible tube breaks during use, it can be partially replaced.

While the invention has been described by reference to specific embodiments chose for purposes of illustration, it should be apparent that numerous modifications could be made thereto by those skilled in the art without departing from the basic concept and scope of the invention.

We claim:

1. A flexible tube of an endoscope which forms an outer wall of an insert part and which is fitted with a built-in object extending along substantially the entire length of said flexible tube, said built-in object including an image guide fiber bundle for transmitting an observed image from the distal end of said insert part to the proximal end thereof, said flexible tube comprising:
   a plurality of flexible tube elements; and
   means for connecting together each pair of adjacent flexible tube elements while said built-in object is inserted therein to form said flexible tube.

2. A flexible tube of an endoscope according to claim 1 wherein said connecting means is rigidly provided on each end portion of each of said flexible tube elements.

3. A flexible tube of an endoscope according to claim 1 wherein said connecting means enables each pair of adjacent flexible tube elements to be connected together and disconnected from each other.

4. A flexible tube of an endoscope according to claim 3, wherein said connecting means allows said flexible tube elements to be connected together and disconnected from each other by axially pushing and pulling said connecting means.

5. A flexible tube of an endoscope according to claim 3, wherein said connecting means connects together each pair of adjacent flexible tube elements by thread engagement, so that said flexible tube elements can be connected together and disconnected from each other by rotating said connecting means about the axis of said flexible tube elements.

6. A flexible tube of an endoscope according to claim 1, wherein said connecting means is covered with a skin of each flexible tube element.

7. A flexible tube of an endoscope according to claim 1, wherein said connecting means is provided with means for sealing the joint between adjacent flexible tube elements.

8. A flexible tube of an endoscope according to claim 1, wherein said flexible tube elements vary in hardness from each other.

9. A method of producing a flexible tube of an endoscope which forms an outer wall of an insert part and which is fitted with a built-in object, said built-in object including an image guide fiber bundle for transmitting an observed image from the distal end of said insert part to the proximal end thereof, comprising the steps of:
   inserting said built-in object into a plurality of flexible tube elements, so that said built-in object extends substantially along the entire length of said plurality of flexible tube elements; and
   connecting together each pair of adjacent flexible tube elements by use of connecting means, while said built-in object is inserted therein, to form a single flexible tube.

10. A method of producing a flexible tube of an endoscope according to claim 9, comprising said connecting rigidly providing means on each end portion of each of said flexible tube elements.

11. A method of producing a flexible tube of an endoscope according to claim 9, comprising connecting together and disconnecting from each other said flexible tube elements by axially pushing and pulling said connecting means.

12. A method of producing a flexible tube of an endoscope according to claim 9, connecting together each pair of adjacent flexible tube elements by thread engagement, so that said flexible tube elements can be connected together and disconnected from each other by rotating said connecting means about the axis of said tube elements.

13. A method of producing a flexible tube of an endoscope according to claim 9, wherein, after said adjacent flexible tube elements are connected together by said connecting means, covering said connecting means with skins of said flexible tube elements.

14. A flexible tube which has a spiral tube inside thereof and which is fitted with a built-in object, comprising:
   a plurality of flexible tube elements; and
   means for connecting together each pair of adjacent flexible tube elements with said built-in object inserted therein to form said flexible tube.

15. A flexible tube of an endoscope which forms an outer wall of an insert part and which is fitted with a built-in object extending along substantially the entire length of said flexible tube, said flexible tube comprising:
   a plurality of flexible tube elements; and
   means for connecting together each pair of adjacent flexible tube elements while said built-in object is inserted therein to form said flexible tube.

* * * * *

UNITED STATES PATENT AND TRADEMARK OFFICE
CERTIFICATE OF CORRECTION

PATENT NO. : 5,217,002
DATED : June 8, 1993
INVENTOR(S) : Hiroyuki KATSURADA et al.

It is certified that error appears in the above-indentified patent and that said Letters Patent is hereby corrected as shown below:

At column 5, line 51 (claim 2, line 2) insert ---,--- after "1".
At column 5, line 54 (claim 3, line 2) insert ---,--- after "1".

Signed and Sealed this

Twenty-ninth Day of August, 1995

Attest:

BRUCE LEHMAN

Attesting Officer     Commissioner of Patents and Trademarks